(12) United States Patent
Song et al.

(10) Patent No.: US 7,736,287 B2
(45) Date of Patent: Jun. 15, 2010

(54) ROTARY METHOD FOR FORMING A VAGINAL APPLICATOR

(75) Inventors: Limin Song, Blue Ash, OH (US); Steven Ray Gilbert, Fairfield, OH (US); Scott Albert Davis, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 195 days.

(21) Appl. No.: 12/146,779

(22) Filed: Jun. 26, 2008

(65) Prior Publication Data

US 2009/0321992 A1 Dec. 31, 2009

(51) Int. Cl.
 *B31B 1/28* (2006.01)
(52) U.S. Cl. ........................ 493/156; 493/160
(58) Field of Classification Search ................ 493/152, 493/154, 155, 156, 158, 159, 160, 161; 604/11, 604/14, 15
See application file for complete search history.

(56) References Cited

U.S. PATENT DOCUMENTS

| | | | | |
|---|---|---|---|---|
| 2,703,042 | A * | 3/1955 | Goodwin | ............... 493/160 |
| 3,568,577 | A * | 3/1971 | Voss et al. | ............... 493/156 |
| 3,683,759 | A | 8/1972 | Voss et al. | |
| 3,696,812 | A | 10/1972 | Jaycox | |
| 4,412,833 | A | 11/1983 | Wiegner et al. | |
| 5,330,421 | A | 7/1994 | Tarar et al. | |
| 5,389,068 | A | 2/1995 | Keck | |
| 5,571,540 | A | 11/1996 | Weyenberg et al. | |
| 5,792,096 | A | 8/1998 | Rentmeester et al. | |
| 5,800,377 | A * | 9/1998 | Campion et al. | ............... 604/15 |
| 5,891,081 | A * | 4/1999 | McNelis et al. | ............... 604/15 |
| 5,909,884 | A | 6/1999 | Schwankhart | |
| 6,171,682 | B1 | 1/2001 | Raidel et al. | |
| 6,264,626 | B1 | 7/2001 | Linares et al. | |
| 6,302,861 | B2 * | 10/2001 | Tweddell et al. | ............... 604/15 |
| 6,358,223 | B1 | 3/2002 | Mackay et al. | |
| 6,368,442 | B1 | 4/2002 | Linares et al. | |
| 6,458,064 | B1 | 10/2002 | Balzar et al. | |
| 6,582,389 | B2 | 6/2003 | Buzot | |
| 6,685,787 | B2 | 2/2004 | Linares et al. | |
| 7,066,870 | B2 | 6/2006 | Fedyk et al. | |
| 2005/0020964 | A1 | | 1/2005 | Melvin et al. |
| 2008/0228128 | A1 | | 9/2008 | Karapasha et al. |

* cited by examiner

*Primary Examiner*—Louis K Huynh
(74) *Attorney, Agent, or Firm*—James E. Oehlenschlager; Gary J. Foos

(57) ABSTRACT

A rotary method for forming a vaginal applicator. The method includes the steps of providing a forming mandrel, an applicator tube, and die then arranging the forming mandrel to be inside the applicator tube and then engaging the forming mandrel and the applicator tube with the die. The forming mandrel has a first sustaining ridge having a circumferential length and a second sustaining ridge having a circumferential length. The circumferential length of the first sustaining ridge is less than the circumferential length of the second sustaining ridge.

14 Claims, 9 Drawing Sheets

ROTARY METHOD FOR FORMING A VAGINAL APPLICATOR

FIELD OF THE INVENTION

The invention relates to a method for forming a vaginal applicator.

BACKGROUND OF THE INVENTION

Feminine care products, such as tampons and pessaries, are generally used by women within the vagina for feminine needs, such as, e.g., to absorb menstrual or other body exudates, for pelvic support, and/or for other feminine needs. Such feminine products can be inserted into the vagina digitally, such as, e.g., by using a finger, or can be inserted into the vagina by using an applicator.

Applicators typically can comprise an applicator tube and a plunger. The material to be expelled from the applicator tube, such as an absorbent tampon or pessary, can be positioned within the insertion member. The insertion member can have a first end for insertion of the material and a second end for receipt of the plunger. To use the applicator, the consumer will grasp the insertion member, position the first end appropriately, such as, e.g., into the body, and move the plunger in the insertion member towards the first end to insert the material. Some applicators can also include a finger grip configuration that is located on the insertion member, which can allow the consumer to more securely hold the applicator during insertion of a material into the body cavity. Various finger grip configurations have been utilized to facilitate the handling of the applicator and to improve the insertion experience.

One finger grip configuration that can be useful is one having raised portions that circumscribe the applicator. For instance the applicator may have one circumscribing ring that is disposed generally perpendicularly to the longitudinal axis of the applicator about the entire circumference of the applicator. Other raised portions may be parts of rings that partially circumscribe the applicator and are generally perpendicular with the longitudinal axis of the applicator.

Such an arrangement can be difficult to manufacture using a rotary process that employs a mandrel and die if there are both a raised portion that completely circumscribes the tampon applicator and raised portions that partially circumscribe the tampon applicator that are disposed close to one another along a common circumference. The difficulty arises because to form the raised portion that completely circumscribes the tampon applicator, the die and forming mandrel must move relative to one another at least a distance equal to the outer circumference of the applicator tube. To ensure a well formed raised portion that a consumer will be unable to identify where on the applicator tube the forming mandrel and die first engaged with one another, the forming mandrel and die should move relative to one another a distance slightly greater that the outer circumference of the applicator tube. Such an approach results in a slightly over formed raised portion in which a small portion of the circumference of the applicator is impressed twice. Ideally, the portion of the applicator that is formed twice is not detectable by the consumer, which should be an aesthetically pleasing result.

Over forming the applicator in such a manner can result in malformation of partially circumscribing raised portions that are disposed close to one another along a common circumference. The malformation can be that some raised portions are longer than others or incomplete raised portions may be formed. Furthermore, if multiple equal length partially circumscribing raised portions disposed about a common circumference wherein the raised portions are separated from one another by a distance less than the magnitude of over forming desired to meet aesthetic constraints, over forming may not be a viable approach to form the applicator.

With these limitations in mind, there is a continuing unaddressed need for a method for forming a vaginal applicator that permits over forming a continuous raised portion about a circumference of the applicator yet still can produce an applicator having intermittent raised portions disposed close to one another along a common circumference.

SUMMARY OF THE INVENTION

A method for forming a vaginal applicator is disclosed. The method comprises the steps of providing a forming mandrel, an applicator tube, and die then arranging the forming mandrel to be inside the applicator tube and then engaging the forming mandrel and the applicator tube with the die. The applicator tube has an applicator tube inner surface having an applicator tube inner circumference and an applicator tube outer surface opposing the applicator tube inner surface. The applicator tube outer surface has an applicator tube outer circumference. The forming mandrel has a longitudinal axis and a forming mandrel circumference about the longitudinal axis of the forming mandrel. The forming mandrel comprises a first sustaining ridge and a second sustaining ridge, each of which is disposed at least partially circumferentially about the forming mandrel. The first sustaining ridge has a circumferential length L1 measured about the forming mandrel circumference. The second sustaining ridge has a circumferential length L2 measured about the forming mandrel circumferential. The first sustaining ridge has an initiation end and a finish end. The first sustaining ridge is radially spaced away from the second sustaining ridge. L1 is less than L2. L2 minus L1 equals the applicator tube inner circumference minus the forming mandrel circumference. L1 is greater than or equal to the applicator tube inner circumference minus the forming mandrel circumference. L1 is at least one-half L2. The forming mandrel circumference is less than the applicator tube inner circumference. The die comprises one or more grooves sized and dimensioned to engage with the first sustaining ridge and the second sustaining ridge. The forming mandrel, applicator tube, and die are engaged with one another such that the forming mandrel, the applicator tube, and the die first engage with one another near the initiation end of the first sustaining ridge and the applicator tube outer surface and die are moved relative to one another while maintaining engagement of the forming mandrel, the applicator tube, and the die such that the applicator tube outer surface and the die travel relative to one another in a direction from the initiation end of the first sustaining ridge towards and beyond the finish end of the first sustaining ridge a tangential distance of at least the applicator tube outer circumference and not more than the applicator tube outer circumference plus L1.

DETAILED DESCRIPTION OF THE INVENTION

Figure 1:
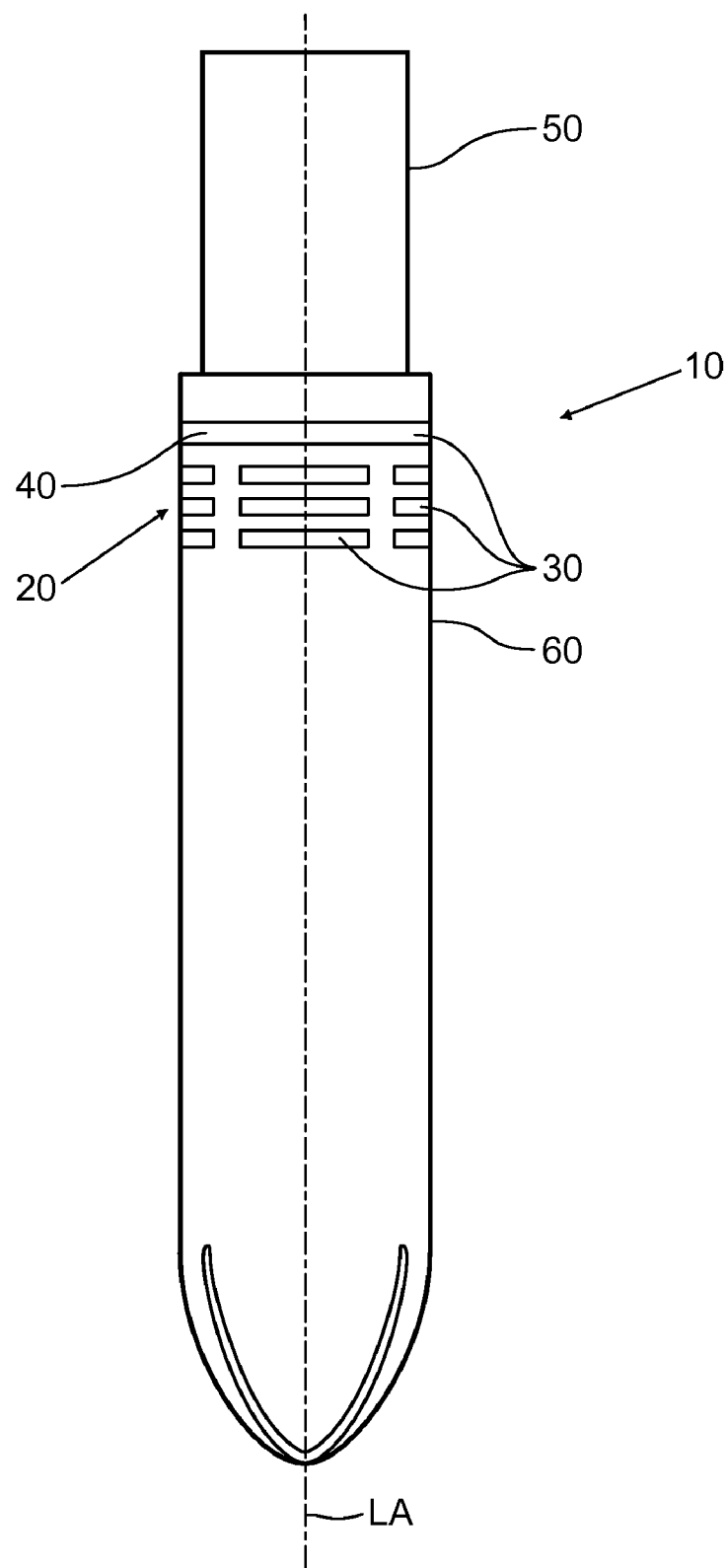
FIG. 1 is an illustration of a vaginal applicator.

FIG. 1 is an illustration of a vaginal applicator 10 having applicator longitudinal axis LA, a gripping region 20, a plurality of raised portions 30, and a plunger 50. The applicator 10 can have at least one continuous raised portion 40, a continuous raised portion 40 being a subset of the class of raised portions 30. The applicator 10 may be formed from an applicator tube 60, the applicator tube 60 being a material including, but not limited to, cardboard, plastic, or other readably formable material. The vaginal applicator 10 can be a tampon applicator. The vaginal applicator 10 can be pessary applicator.

Figure 2:
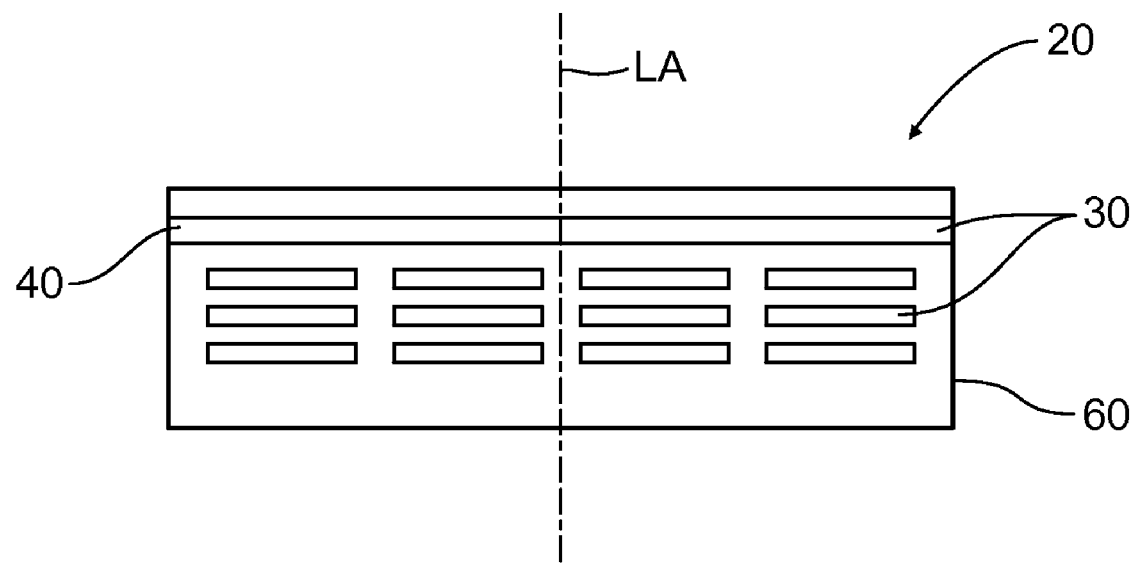
FIG. 2 is an illustration of a gripping region of a vaginal applicator.

FIG. 2 is an illustration of an entire circumference of a gripping region 20. As illustrated in FIG. 2, in some embodiments, a plurality of raised portions 30 having equal length about the circumference of the applicator 10 and aligned along a common circumference at a particular location relative to the applicator longitudinal axis LA may be desirable.

Figure 3:
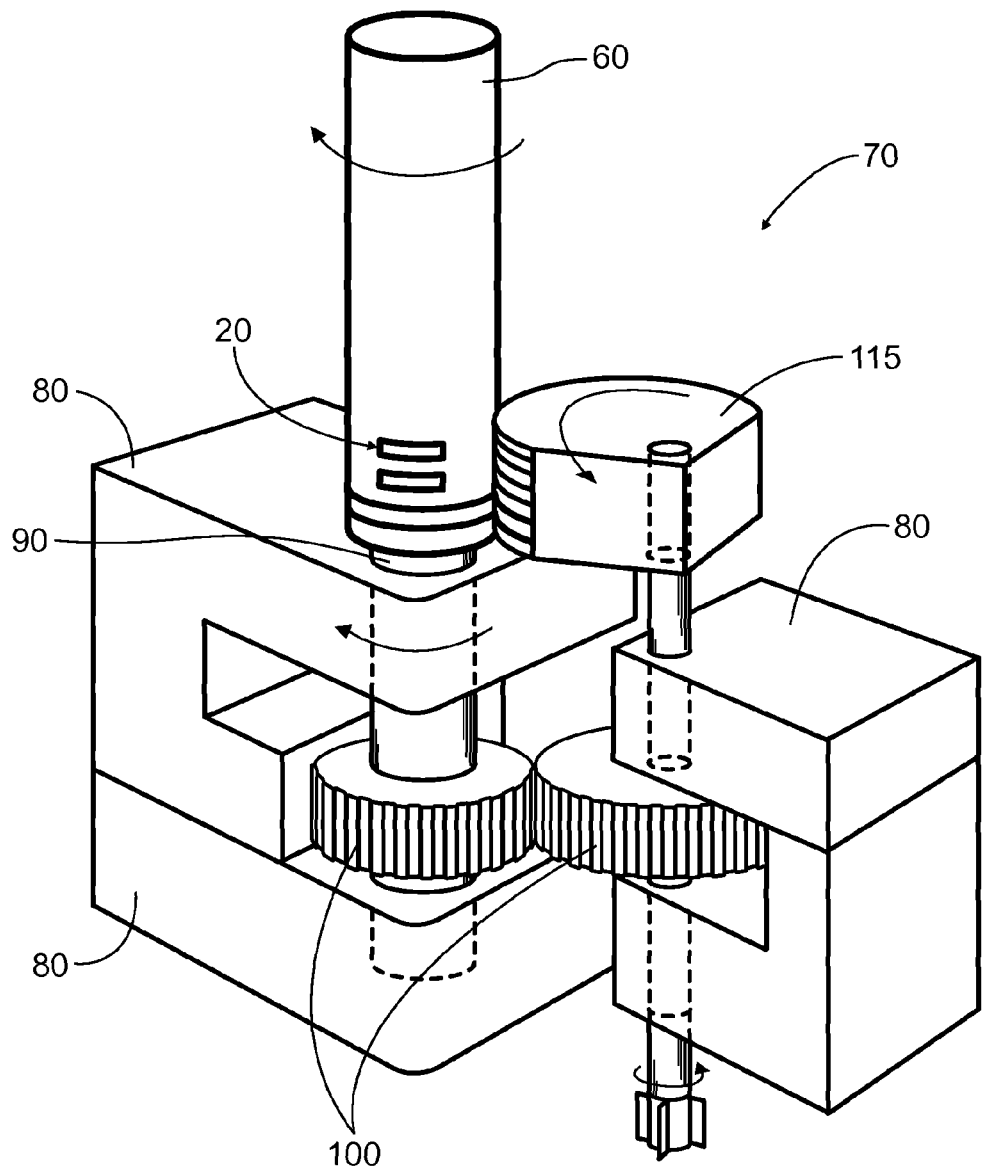
FIG. 3 is an illustration of a forming apparatus for forming a vaginal applicator.

A forming apparatus 70 for impressing the desired patterned gripping region 20 is illustrated in FIG. 3. The forming apparatus 70 can comprise guide bushings 80, a forming mandrel 90, drive gears 100, and die 115. Mandrel 90 and die 115 can move rotationally counter to one another (i.e. one can rotate counterclockwise and the other can rotate clockwise so that the mandrel 90 and die 115 have a tangential velocity in the same direction where the two are operatively engaged with one another), thereby deforming the applicator tube 60 into the desired shape. Mandrel 90 and die 115 can move rotationally counter to one another at the same magnitude of angular velocity. The forming mandrel 90 can have topography that corresponds to the desired topography of the gripping region 20 of the applicator 10. The forming apparatus 70 can comprise addition parts or be configured to load the unformed applicator tube 60 and unload the formed applicator tube 60 after the pattern for the gripping region 20 is imparted thereon. As illustrated in FIG. 3, the applicator tube 60 is squeezed in the nip between the forming mandrel 90 and die 115 rotating counter to one another to impart texture to the applicator tube 60. The rotational arrows in FIG. 3 indicate the direction of rotation of the relevant parts in one embodiment, other arrangements being possible. The applicator tube 60 need not rotate entirely concert with the forming mandrel 90 if the applicator tube 60 has a diameter that is greater than the diameter of the forming mandrel 90. The applicator tube 60 may have a diameter that is slightly larger than the diameter of the forming mandrel 90 so as to provide for easy loading and unloading of the applicator tube 60. In such an arrangement the applicator tube 60 and forming mandrel 90 will move relative to one another in a manner similar to how a planet carrier gear moves relative to an annulus gear in a planetary gearing system.

Figure 4:
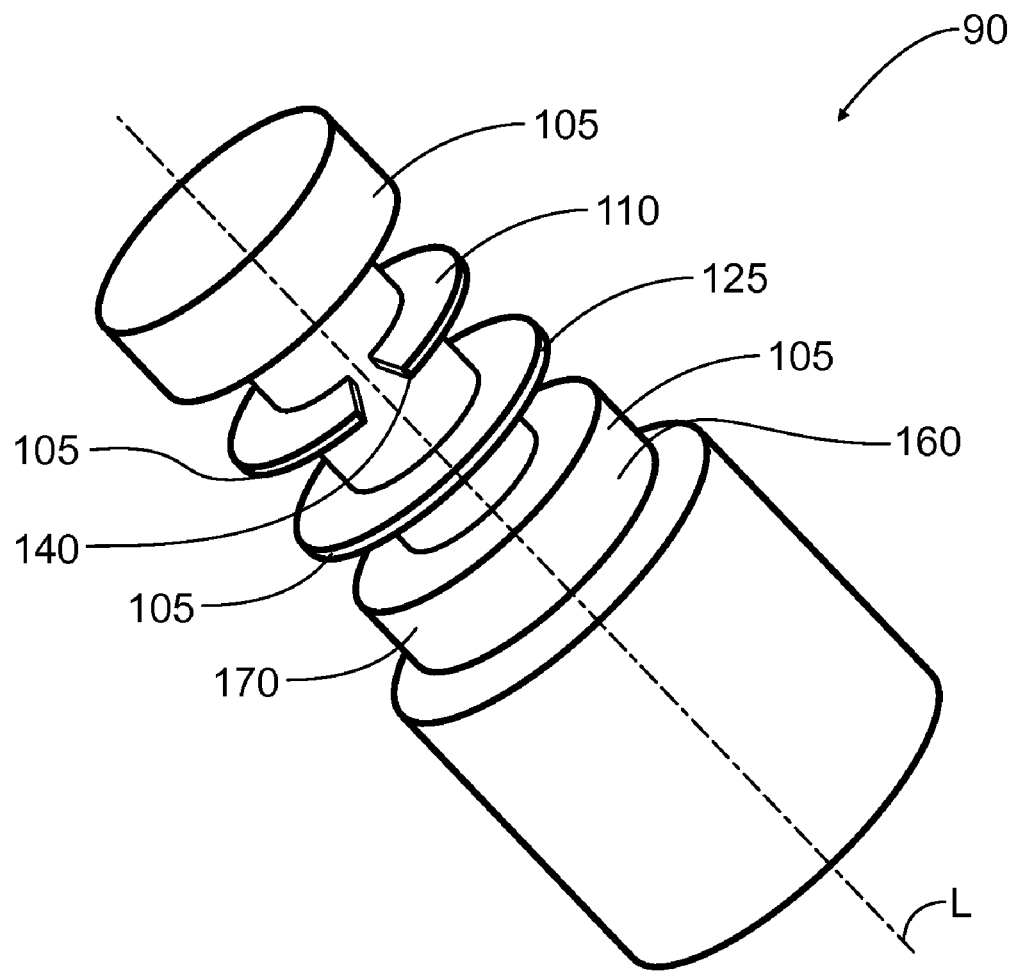
FIG. 4 is an illustration of a forming mandrel.

FIG. 4 is an illustration of a forming mandrel 90 having longitudinal axis L and a forming mandrel circumferential periphery 105 about the longitudinal axis L of the forming mandrel 90. The forming mandrel 90 can comprise a first sustaining ridge 110, a second sustaining ridge 120, and a third sustaining ridge 125. The first sustaining ridge 110, second sustaining ridge 120, and third sustaining ridge 125 can each be disposed circumferentially about the forming mandrel 90 or partially circumferentially (i.e. about part of the circumference of the forming mandrel 90). The first sustaining ridge 110 and second sustaining ridge 120 can be generally aligned with one another circumferentially about the forming mandrel 90 (i.e. generally lying about a common circumference of the forming mandrel 90). The first sustaining ridge 110 and second sustaining ridge 120 can be spaced axially away from one another along the longitudinal axis L of the forming mandrel 90, axially away referring to the location relative to the longitudinal axis L of the forming mandrel 90. The first sustaining ridge 110 can be configured to extend about a portion of the circumferential periphery 105 of the forming mandrel 90. The second sustaining ridge 120 can be configured to extend about a portion of the circumferential periphery 105 of the forming mandrel 90. The third sustaining ridge 125 can be configured to extend about the entire circumferential periphery 105 of the forming mandrel 90. The third sustaining ridge 125 can be spaced axially away from the first sustaining ridge 110 and the second sustaining ridge 120.

In some embodiments, the forming mandrel 90 can have a seating portion 160 extending about the longitudinal axis L of the forming mandrel 90. The seating portion 160 can have a circumferential periphery 105 which is defined by the surface of the seating portion 160 about the longitudinal axis L of the forming mandrel 90. The circumferential periphery 105 can be a circle, generally circular, oval shape or any other shape that is operable with respect to a rotary mandrel/die forming apparatus. That is, the word circumference, and derivatives thereof, is used to refer to a periphery generally orthogonal to the longitudinal axis L and is not limited to circular shapes.

The length of the circumferential periphery 105 measured orthogonal to the longitudinal axis L of the forming mandrel 90 is the forming mandrel circumference 170. The sustaining ridges can be sized and dimensioned such that they lie at or within the circumferential periphery 105 when viewed along the longitudinal axis L of the forming mandrel 90.

Figure 5:
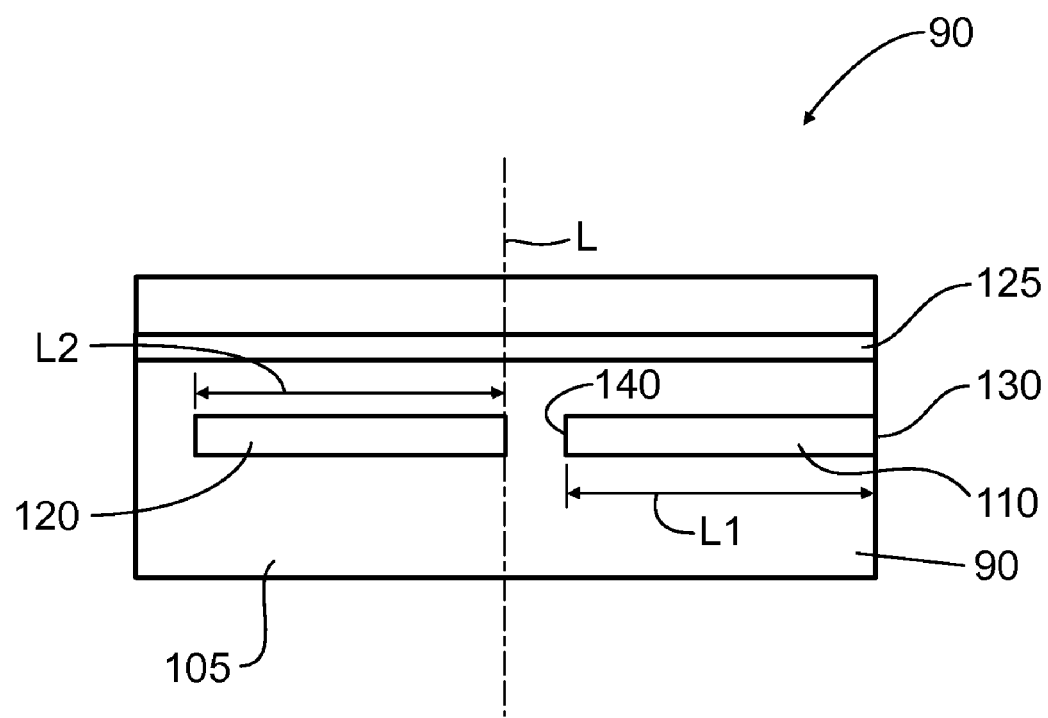
FIG. 5 is an illustration of the entire forming mandrel circumference.

FIG. 5 is an illustration of the entire circumferential periphery 105 of a forming mandrel 90. The first sustaining ridge 110 can have an initiation end 130 and a finish end 140. The initiation end 130 corresponds to that portion of the first sustaining ridge 110 that initiates support of the applicator tube 60 as the forming mandrel 90 and die 115 move relative to one another. The finish end 140 corresponds to the portion of the first sustaining ridge 110 which last supports the applicator tube 60 against being deformed by the die 115 to be generally conforming with the surface contour, defined by the first sustaining ridge 110, second sustaining ridge 120, third sustaining ridge 125, and any additional sustaining ridges or like features of the forming mandrel 90. For the first sustaining ridge 110, the initiation end 130 and finish end 140 depends on the direction that forming mandrel 90 and die 115 move relative to one another. The forming mandrel 90 can have one or more additional sustaining ridges between the first sustaining ridge 110 and the second sustaining ridge 120 sized, dimensioned, and arranged to provide for the desired surface texture of the gripping region 20 of applicator tube 60 that form applicator 10.

As illustrated in FIG. 5, first sustaining ridge 110 has a circumferential length L1 measured about the forming mandrel circumferential periphery 105. The second sustaining ridge 120 has a circumferential length L2 measured about the forming mandrel circumferential periphery 105. The third sustaining ridge 125 can extend about the entire circumferential periphery 105 of the forming mandrel 90. The third sustaining ridge 125 can extend at least partially circumferentially about the forming mandrel 90. The third sustaining ridge 125 can be located axially away from the first sustaining ridge 110 and second sustaining ridge 120.

Figure 6:
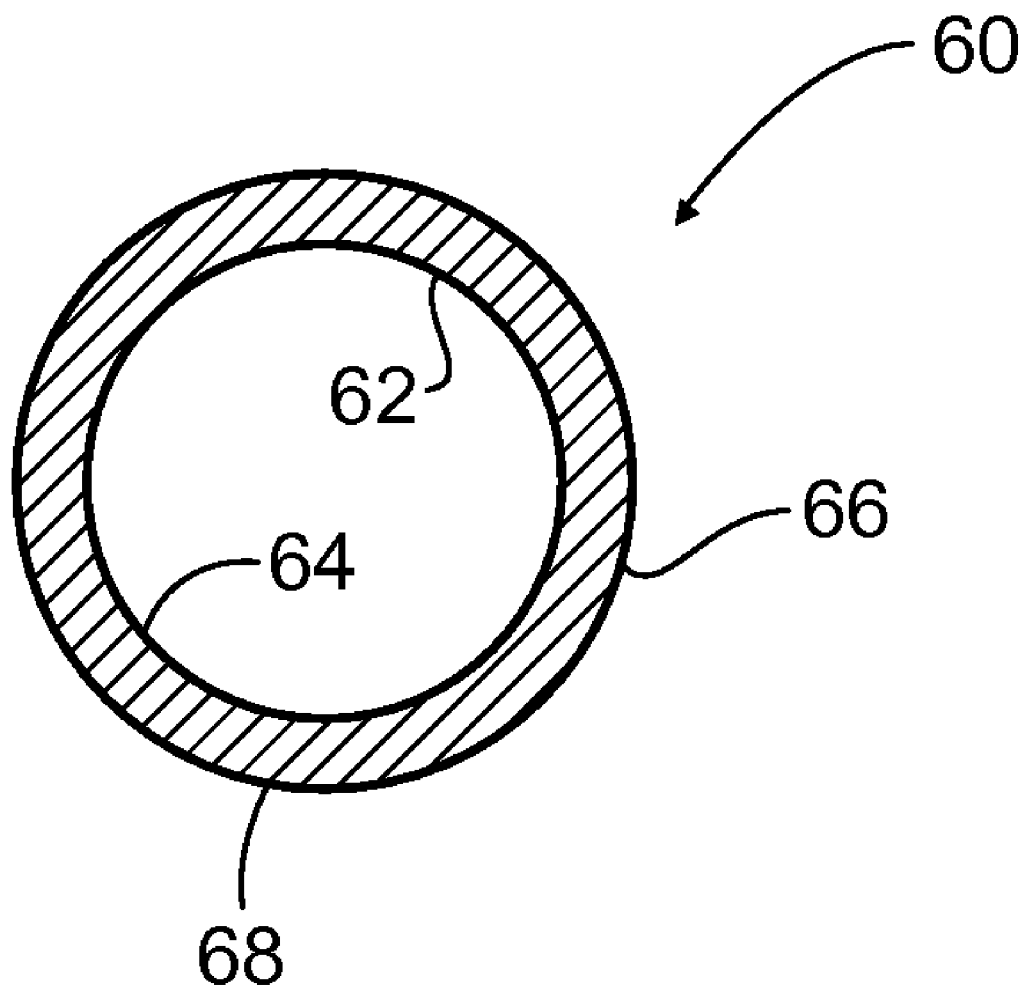
FIG. 6 is an illustration of a cross section of an applicator tube.

A cross section of applicator tube 60 is illustrated in FIG. 6. Applicator tube 60 has an applicator tube inner surface 62 having an applicator tube inner circumference 64 (measured in a portion of the applicator tube that has not been deformed by the forming method). The applicator tube 60 has applicator tube outer surface 66 which is the exterior surface of the applicator tube 60 opposing the applicator tube inner surface 62. The applicator tube outer surface 66 has an applicator tube outer circumference 68 which is the circumference of the applicator tube 60 measured orthogonal to the longitudinal axis LA of the applicator tube 60.

Figure 7:
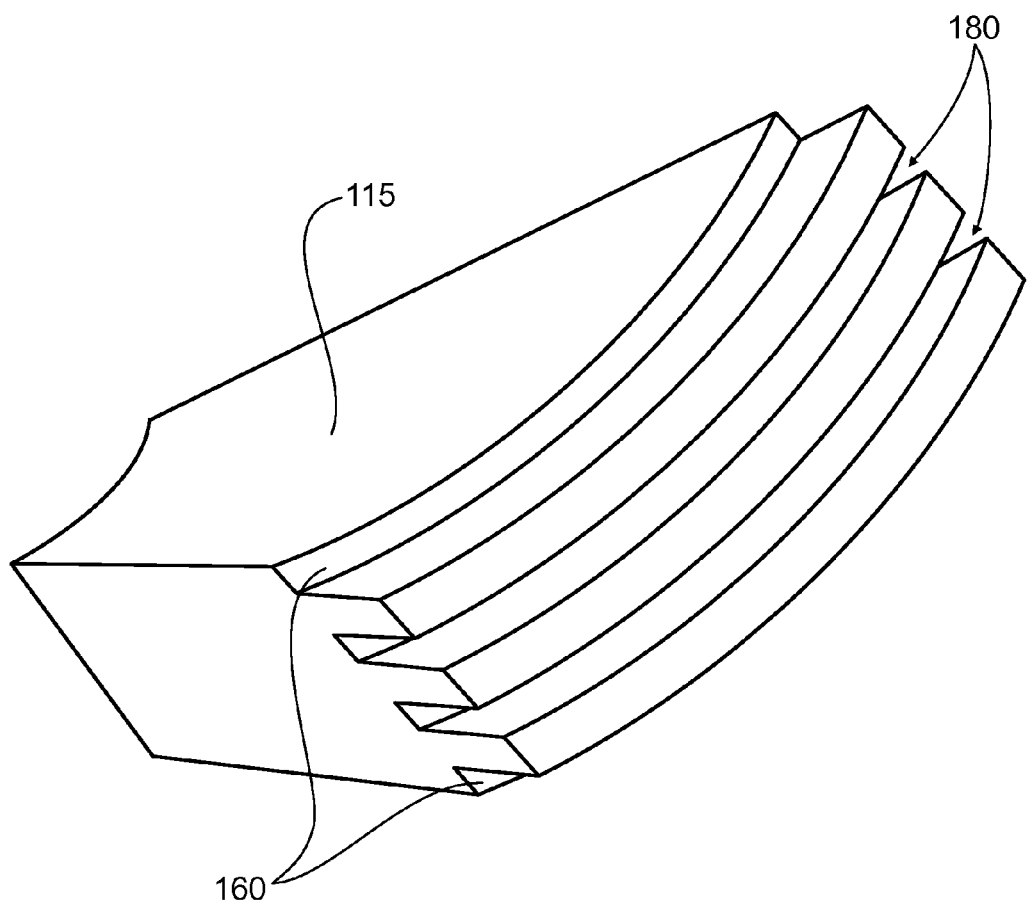
FIG. 7 is an illustration of a die.

A schematic of an embodiment of a die 115 is illustrated in FIG. 7. As illustrated in FIG. 7, die 115 comprises one or more grooves 180 sized and dimensioned to engage with the first sustaining ridge 110 and second sustaining ridge 120. The die 115 can also have one or more seating portions 160 sized and dimensioned to operatively engage with the seating portion 160, or seating portions 160, of the forming mandrel 90. Seating portions 160 may not be necessary provided that the forming mandrel 90 and die 115 are mounted rigidly in the forming apparatus 70. Die 115 can have any shape such that it is sized and dimensioned to engage with the forming mandrel 90 and raised portions disposed thereon.

To form the vaginal applicator 10, a forming mandrel 90, as described above, is provided along with an applicator tube 60, and die 115. The forming mandrel 90 is arranged such that the forming mandrel 90 is inside the applicator tube 60. The forming mandrel 90 and applicator tube 60 are engaged such that the forming mandrel 90, applicator tube 60, and die 115 first engage with one another at or near the initiation end 130 of the first sustaining ridge 110. The applicator tube outer surface 66 and die 115 are moved relative to one another while maintaining engagement of the forming mandrel 90, applicator tube 60, and the die 115 such that the applicator tube outer surface 66 and the die 115 travel relative to one another in a direction from the initiation end 130 of the first sustaining ridge 110 towards and beyond the finish end 140 of the first sustaining ridge 110 a tangential distance of at least applicator tube outer circumference 68 but not more than the applicator tube outer circumference 68 plus the circumferential length L1 of the first sustaining ridge 110. By forming in such a manner, the first sustaining ridge 110 and second sustaining ridge 120 support the applicator tube 60 as the die 115 impresses the desired grip pattern upon the gripping region 20 of the vaginal applicator 10.

If the applicator tube outer surface 66 and die 115 only move relative to one another a tangential distance less than the applicator tube outer circumference 68, the applicator tube 60 will be under formed as the entire circumferential periphery 105 forming mandrel 90 will not be engaged with the die 115 to impart the desired texture to the applicator tube 60. More simply stated, the die will not impress about the entire outer circumference 68 of the applicator tube 60. If the applicator tube outer surface 66 and die 115 move relative to one another a tangential distance greater than the applicator tube outer circumference 68 plus the circumferential length L1 of the first sustaining ridge 110, the applicator tube 60 will be over formed because too much of the first sustaining ridge 110 will encounter the applicator tube 60 at second time. The result will be that the raised portion 30 sustained by the first sustaining ridge 110 will be longer than intended because trailing end of the raised portion 30 will be formed twice. Such an arrangement can result in an aesthetically unpleasing result.

The forming mandrel 90 and applicator tube 60 are engaged such that the forming mandrel 90, applicator tube 60, and die 115 first engage with one another near the initiation end 130 such that the initiation end 130 of the first sustaining ridge 110 supports the applicator tube 60 when engaging the forming mandrel 90, applicator tube 60, and die 115 with one another.

The general approach of the method described herein is commonly referred to in the art as a rotary method. The rotary method is a compact and efficient method for forming vaginal applicators that can be practically used on a commercial scale. The method described herein can be useful for forming a vaginal applicator 10 having a continuous raised portion 40 and one or more raised portions 30, each having the same length, that are closely spaced from one another along a common circumference of the vaginal applicator 10.

One problem sometimes associated with forming a vaginal applicator 10 having a continuous raised portion 40 using a rotary method is that the desired continuous raised portion 40 may be incompletely formed. That is, the desired continuous raised portion 40 may end up being a raised portion 30 that does not quite extend around the entire applicator tube outer surface 66. Such an arrangement may not be aesthetically pleasing. Furthermore, by having a continuous raised portion 40 formed by a rotary method, there is a corresponding impressed portion of the applicator tube 60 that has an inner diameter that can be sized and dimensioned to restrain a plunger 50 lying coaxially within the applicator tube 60, the plunger 50 having a flared portion that can operatively engage with an impressed portion of the applicator tube 60. If this raised portion 40 is incompletely formed, the plunger 50 may not be adequately restrained.

To ensure that a continuous raised portion 40 is formed, the applicator tube outer surface 66 and die 115 can be moved relative to one another while maintaining engagement of the forming mandrel 90 such that the applicator tube outer surface 66 and die 115 travel relative to one another a tangential distance greater than the applicator tube outer circumference 68. By doing so, at least a portion of the continuous raised portion 40 is impressed upon the forming mandrel 90 twice, which is referred to herein as over forming. Over forming can be a desirable approach for forming a continuous raised portion 40 because the resulting raised portion 40 can be more aesthetically pleasing.

One limitation that can be imposed by such over forming of the applicator tube 60 is that if there are a plurality of raised portions 30, each having the same length, that are closely spaced from one another along a common circumference of the vaginal applicator 10, the raised portions 30 should not be any closer together than the extent of over forming of the continuous raised portion. This constraint may reduce the options designers of vaginal applicators 10 have to design vaginal applicators 10 having intermittent raised portions 30 that have a common length. Furthermore, if the first sustaining ridge 110 and second sustaining ridge 120 have the same length, the raised portions 30 on the applicator tube 60 resulting from formation thereon will not end up having the same length, which may not be functionally or aesthetically pleasing to the user of the vaginal applicator 10.

There are several constraints that can provide for over forming the continuous raised portion 40 and forming a plurality of raised portions 30 having an equal length that are spaced closely together about a common circumference of the vaginal applicator 10. The forming mandrel 90 can be sized and dimensioned such that the circumferential length L1 can be less than the circumferential length L2. The circumferential length L2 minus the circumferential length L1 can be about equal to the applicator tube inner circumference 64 minus the forming mandrel circumference 170. Such dimensioning of the relevant parts helps to ensure that the raised portions 30 formed by the first sustaining ridge 110 and second sustaining ridge 120 have the same circumferential length.

The circumferential length L1 can be greater than or equal to the applicator tube inner circumference 64 minus the forming mandrel circumference 170. The circumferential length L1 can be sized and dimensioned such that circumferential length L1 is at least one-half circumferential length L2. In such an arrangement, as the applicator tube 60 is impressed upon the mandrel 90 by the die 115 to form the desired grip pattern, the applicator tube 60 will encounter the entire length of the first sustaining ridge 110 once as the die 115 and applicator tube 60 move relative to one another. As the applicator tube 60 is over formed to ensure that a continuous raised portion 40 is formed on the applicator tube 60, the applicator tube 60 will again encounter the initiation end 130 of the first sustaining ridge 110 and the applicator tube 60 will be impressed upon the first sustaining ridge 110 for some length but not beyond the length impressed upon during the first pass of the first sustaining ridge 110.

Figure 8:
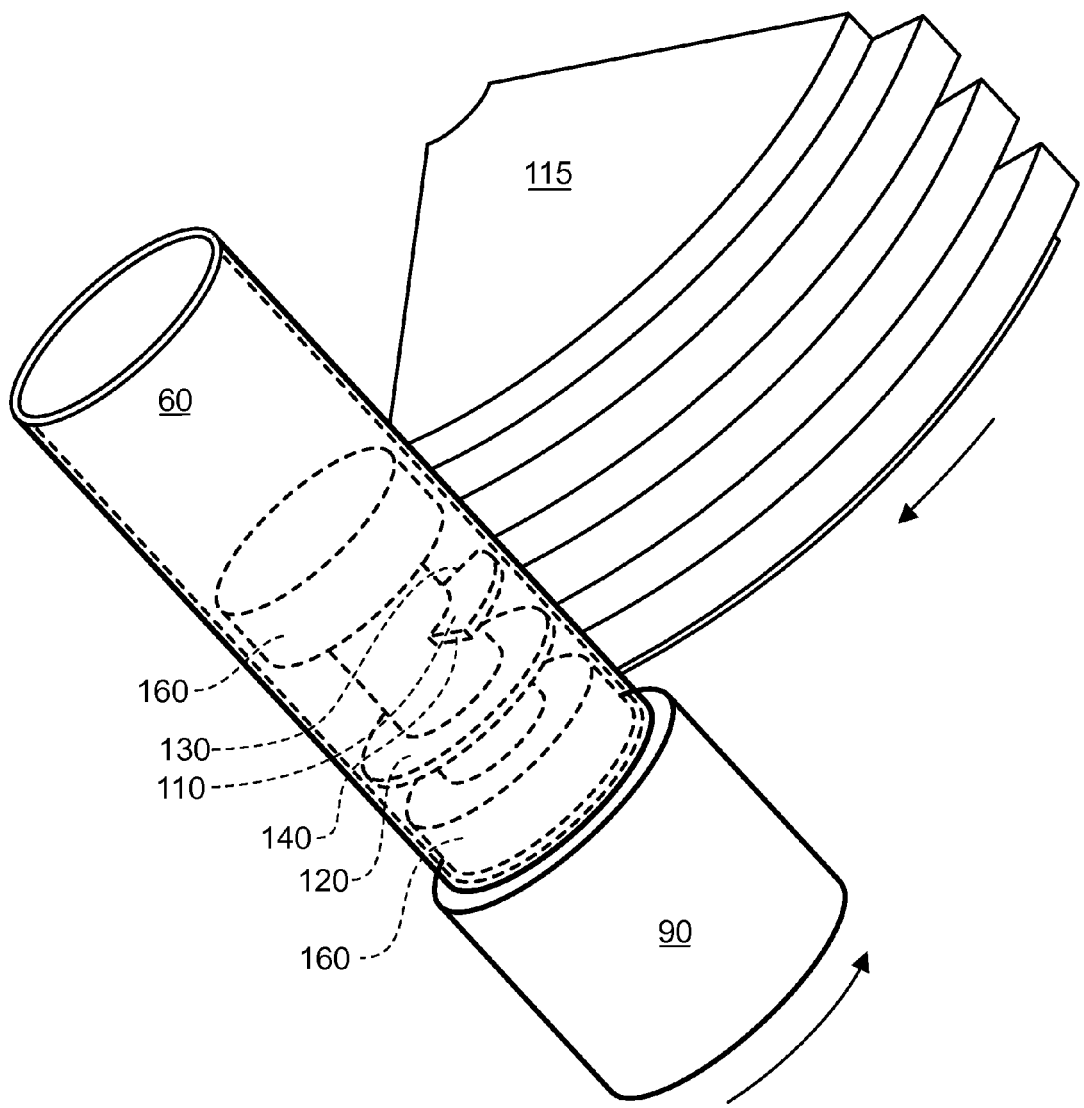
FIG. 8 is an illustration of a forming mandrel, applicator tube, and die engaged for forming the vaginal applicator.

There are a variety of approaches for providing relative movement between the die 115 and the applicator tube outer surface 66. For instance the die 115 can be stationary and the forming mandrel 90 and applicator tube 60 engaged therewith are rotated along the grooves 180 of die 115. In such an arrangement, the longitudinal centerline L of the forming mandrel 90 would move relative to the die 115. The longitudinal centerline L of forming mandrel 90 can remain stationary and the forming mandrel 90 can be rotated. The longitudinal centerline L of the forming mandrel 90 can remain fixed and the forming mandrel 90 can be fixed rotationally and the die 115 can travel about the forming mandrel 90. The forming mandrel 90 and the die 115 can move rotationally relative to one another in counter directions, as indicated in FIG. 8.

To allow the applicator tube 60 to be loaded on the forming mandrel 90 the forming mandrel circumference 170 can be less than the applicator tube inner circumference 64.

Figure 9:
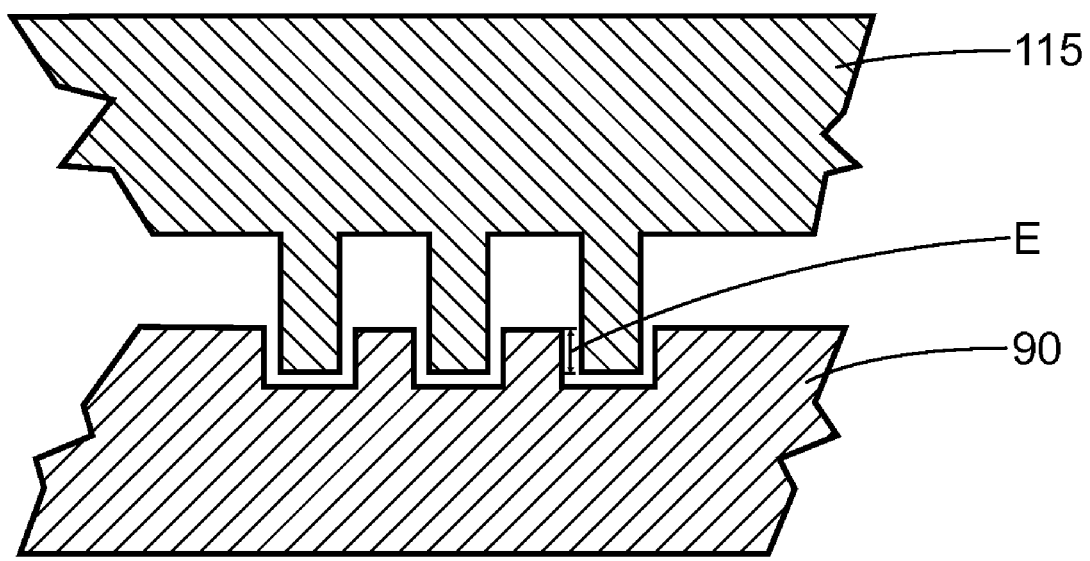
FIG. 9 is an illustration of a portion of a die and a portion of a forming mandrel engaged with one another.

To impress the applicator tube 60, the die 115 and forming mandrel 90 can be engaged with one another to a depth of engagement E, as illustrated in FIG. 9. The forming mandrel 90 and applicator tube 60 can be engaged with the die 115 such that the applicator tube inner circumference 64 minus the depth of engagement E is greater than or about equal to the forming mandrel circumference 170. For a cardboard applicator tube 60 having a thickness of about 0.5 mm, the depth of engagement E can be about 0.25 mm.

The applicator tube 60 can be constructed from any suitable material. Suitable materials include, for example, and can be selected from the group consisting of paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, poly hydroxyalkanoate, ethylene vinyl acetate, polyurethane, silicone, derivatives thereof, copolymers thereof, and mixtures thereof, or any suitable smooth plastic material. Examples of suitable materials are disclosed in, e.g., U.S. Pat. Nos. 5,346,468 and 5,558,631. In some embodiments, additives can be included in the material to alter or enhance certain material properties. Suitable additives include, for example, mold release agents, slip agents, surface energy modifiers, pearlescent agents, and/or any other suitable additives. In certain embodiments, the applicator tube 60 can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the applicator tube 60 can include a textured surface. Texture can be provided in any suitable manner, such as, e.g., by designing texture into or adding texture to the insertion member.

In some embodiments, the applicator tube 60 can be in the form of a spirally wound, convolutely wound or longitudinally seamed hollow tube, which can be formed from paper, paperboard, cardboard or a combination thereof. The applicator tube 60 can have a cellophane coating, a plastic coating, or some other coating to make the applicator tube 60 smooth and slippery. The applicator tube 60 can have one or more walls of any suitable thickness. In certain embodiments, the one or more walls can have a predetermined thickness of from about 0.1 millimeters to about 0.7 millimeter. The wall can be constructed from a single ply of material or can be formed from two or more plies that are bonded together, such as, e.g., to form a laminate. When two or more plies are utilized, some or all of the plies can be spirally wound, convolutely wound or longitudinally seamed to form an elongated cylinder. For example, in certain embodiments the wall can be constructed using a smooth thin ply of material on the outside or exterior surface that surrounds a coarser and possibly thicker ply. In embodiments where the wall contains at least three plies, the middle ply can be the thicker ply and the interior and exterior plies can be smooth and/or slippery to facilitate expulsion of the vaginal device (e.g. tampon or pessary) and to facilitate insertion of the vaginal applicator 10 into the vagina. The wall can contain one to four plies, although more plies can be utilized if desired.

The plies can be held together in any suitable manner, such as, e.g., by one or more adhesives, such as glue, by heat, by pressure, by ultrasonics, or by any other suitable manner for holding the plies together. The adhesive can be either water-soluble or water-insoluble. In certain embodiments, a water-soluble adhesive can be used such that the wall will quickly break apart when it is immersed in water, such as, e.g., by flushing the insertion member down a toilet. Alternatively, the material can be overlapped into a tubular configuration, such as, for example, by spirally or convolutely winding the insertion member into a cylindrical tube. In the case of other applicator tube 60 construction methods, such as fiber or plastic molding, or integral tube forming (e.g., thermoforming plastic), no seams may be present and the corrugations can optionally be formed as part of the tube molding or forming process. Suitable materials and dimensions for applicator tube 60 include the applicator deployed in TAMPAX, tampon and applicator products having a cardboard flushable applicator, marketed by Procter & Gamble Co., Cincinnati, Ohio.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming a vaginal applicator comprising the steps of:
   a. providing a forming mandrel, an applicator tube, and die;
      wherein said applicator tube has an applicator tube inner surface having an applicator tube inner circumference and an applicator tube outer surface opposing said applicator tube inner surface, said applicator tube outer surface having an applicator tube outer circumference;
      wherein said forming mandrel has a longitudinal axis and a forming mandrel circumference about said longitudinal axis of said forming mandrel;
      wherein said forming mandrel comprises a first sustaining ridge and a second sustaining ridge, each of which is disposed at least partially circumferentially about said forming mandrel;
      wherein said first sustaining ridge has a circumferential length L1 measured about said forming mandrel circumference;
      wherein said second sustaining ridge has a circumferential length L2 measured about said forming mandrel circumference;
      wherein said first sustaining ridge has an initiation end and a finish end;
      wherein said first sustaining ridge is radially spaced away from said second sustaining ridge;
      wherein L1 is less than L2;
      wherein L2 minus L1 equals said applicator tube inner circumference minus said forming mandrel circumference;
      wherein L1 is greater than or equal to said applicator tube inner circumference minus said forming mandrel circumference;
      wherein L1 is at least one-half L2;
      wherein said forming mandrel circumference is less than said applicator tube inner circumference; and
      wherein said die comprises one or more grooves sized and dimensioned to engage with said first sustaining ridge and said second sustaining ridge;
   b. arranging said forming mandrel to be inside said applicator tube; and
   c. engaging said forming mandrel and said applicator tube with said die such that said forming mandrel, said applicator tube, and said die first engage with one another near said initiation end of said first sustaining ridge and moving said applicator tube outer surface and said die relative to one another while maintaining engagement of said forming mandrel, said applicator tube, and said die such that said applicator tube outer surface and said die travel relative to one another in a direction from said initiation end of said first sustaining ridge towards and beyond said finish end of said first sustaining ridge a tangential distance of at least said applicator tube outer circumference and not more than said applicator tube outer circumference plus L1.

2. The method according to claim 1, wherein said die is stationary.

3. The method according to claim 1, wherein said forming mandrel and said die move rotationally relative to one another.

4. The method according to claim 1, wherein said forming mandrel further comprises a continuous third sustaining ridge spaced axially away from said first sustaining ridge.

5. The method according to claim 1, wherein said first sustaining ridge and said second sustaining ridge are spaced axially away from one another.

6. The method according to claim 1, wherein said first sustaining ridge and said second sustaining ridge are circumferentially aligned with one another.

7. The method according to claim 1, wherein said initiation end of said first sustaining ridge supports said applicator tube when engaging said forming mandrel and said applicator tube with said die.

8. The method according to claim 1, wherein said forming mandrel and said die are engaged with one another at a depth of engagement, wherein said forming mandrel and said applicator tube are engaged with said die such that said applicator tube inner circumference minus said depth of engagement is greater than or equal to said forming mandrel circumference.

9. The method according to claim 1, wherein said applicator tube is cardboard.

10. The method according to claim 1, wherein said applicator tube is paper.

11. The method according to claim 1, wherein said vaginal applicator is a tampon applicator.

12. The method according to claim 1, wherein said vaginal applicator is a pessary applicator.

13. The method according to claim 1, wherein said forming mandrel further comprises a third sustaining ridge spaced axially away from said first sustaining ridge and said second sustaining ridge, wherein said third sustaining ridge extends partially circumferentially about said forming mandrel.

14. The method according to claim 1, wherein said forming mandrel further comprises a third sustaining ridge spaced axially away from said first sustaining ridge and said second sustaining ridge.

* * * * *

UNITED STATES PATENT AND TRADEMARK OFFICE
CERTIFICATE OF CORRECTION

| | | |
|---|---|---|
| PATENT NO. | : 7,736,287 B2 | Page 1 of 1 |
| APPLICATION NO. | : 12/146779 | |
| DATED | : June 15, 2010 | |
| INVENTOR(S) | : Limin Song et al. | |

It is certified that error appears in the above-identified patent and that said Letters Patent is hereby corrected as shown below:

Cover Page
(74) *Attorney, Agent or Firm*
Delete "Gary J. Foos" and insert -- Gary J. Foose --.

Signed and Sealed this
Twenty-second Day of March, 2011

David J. Kappos
*Director of the United States Patent and Trademark Office*